United States Patent

Liu et al.

[11] Patent Number: 6,118,127
[45] Date of Patent: Sep. 12, 2000

[54] DETECTOR HAVING A TRANSMISSION GRATING BEAM SPLITTER FOR MULTI-WAVELENGTH SAMPLE ANALYSIS

[75] Inventors: Changsheng Liu; Qingbo Li, both of State College, Pa.

[73] Assignee: Spectrumedix Corporation, State College, Pa.

[21] Appl. No.: 09/449,418

[22] Filed: Nov. 29, 1999

Related U.S. Application Data

[63] Continuation of application No. 09/084,236, May 26, 1998, Pat. No. 5,998,796.
[60] Provisional application No. 60/068,527, Dec. 22, 1997.

[51] Int. Cl.$^7$ .................................................. G01N 21/64
[52] U.S. Cl. .......................................................... 250/458.1
[58] Field of Search ........................................ 250/458.1

[56] References Cited

U.S. PATENT DOCUMENTS

| | | |
|---|---|---|
| 3,896,312 | 7/1975 | Brown et al. . |
| 3,899,213 | 8/1975 | Fantasia et al. . |
| 4,087,685 | 5/1978 | Froot . |
| 5,112,125 | 5/1992 | Neumann . |
| 5,303,026 | 4/1994 | Strobl et al. . |
| 5,329,353 | 7/1994 | Ichimura et al. . |
| 5,534,703 | 7/1996 | Kambara et al. . |
| 5,713,364 | 2/1998 | DeBaryshe et al. . |
| 5,998,796 | 12/1999 | Liu et al. ............................. 250/458.1 |
| 6,017,434 | 1/2000 | Simpson et al. ........................ 204/612 |

*Primary Examiner*—Constantine Hannaher
*Attorney, Agent, or Firm*—Pennie & Edmonds LLP

[57] ABSTRACT

A detector for DNA sample identification is provided with a transmission grating beam splitter (TGBS). The TGBS split fluoresced light from a tagged DNA sample into 0th order and a 1st order components, both of which are detected on a two-dimensional detector array of a CCD camera. The 0th and 1st order components are detected along a column of pixels in the detector array, and are spaced apart from one another. The DNA samples are tagged with four fluorescent dyes, one dye specific for each nucleotide, and all four dyes responding in slightly different manner to the same monochromatic excitation signal. The TGBS splits fluoresced incoming light into 0th and 1st order components, which are then spread out among a number of pixels in the detector array. The 1st component of this light is received by pixels whose position relative to the 0th order component depends on the frequency of fluorescence. Thus, the position at which signal energy is detected on the array is indicative of the particular dye, and therefore, the corresponding nucleotide tagged by that dye. Monitoring signal energy at the 0th order pixel and selected 1st order pixels, provides a set of data from which one may then identify the particular nucleotide.

13 Claims, 10 Drawing Sheets

DETECTOR HAVING A TRANSMISSION GRATING BEAM SPLITTER FOR MULTI-WAVELENGTH SAMPLE ANALYSIS

RELATED APPLICATIONS

This is a continuation of application Ser. No. 09/084,236, filed May 26, 1998, now U.S. Pat. No. 5,998,796 which claims priority to provisional application No. 60/068,527, filed Dec. 22, 1997.

TECHNICAL FIELD

This invention relates to a detector system for performing sample analysis, such as DNA sequencing, DNA fingerprinting, absorption/emission spectroscopy, and the like. More particularly, it pertains to a detector system which employs a transmission grating beam splitter for separating incoming light, either fluoresced or otherwise emitted from one or more samples, into multiple order diffraction bands and wavelengths.

BACKGROUND

Prior art techniques for detecting fluorescence from a capillary used in DNA sequencing are well known.

Narrowband approaches typically call for filtering the fluoresced light into discrete bands, through the use of discrete filter elements or filter wheels, followed by further processing and comparison of the resulting output. Such approaches are rather limited in the quality and volume of data that can be used for nucleotide identification.

Multi-wavelength approaches, such as that described in Karger, A. et al., Multiwavelength Fluorescense Detection For DNA Sequencing Using Capillary Electrophoresis, Nucleic Acids Research, v. 19, no. 18, pp. 4955–4962, use a spectrometer to separate the light into multiple bands for subsequent analysis. However, spectrometers and the associated equipment used, as shown in FIG. 1 of this reference, are both expensive and bulky. The spectrometer used in this figure typically comprises an entrance slit to spatially limit the incoming light; a collimator lens having a focal point coincident with the position of the entrance slit so as to convert the light emerging from the slit into parallel rays; a reflection diffraction grating to diffract the parallel rays from the collimator lens to produce spectra; and an imaging lens to focus the diffracted parallel rays onto a CCD imaging plane. Thus, the arrangement of FIG. 1 in this reference is expensive, bulky and has low light throughput.

SUMMARY OF THE INVENTION

The present invention provides a detector system which provides the high data volume of the spectrometer, while not incurring its cost, bulkiness and low light throughput. This is realized by means of a device in accordance with the present invention which employs a Transmission Grating Beam Splitter ("TGBS") positioned between a capillary and an array of detector pixels associated with a detector camera. The TGBS spatially splits fluoresced light coming from a fluorophore which has migrated through a capillary into at least a 0th-order and a 1st-order region, at least the latter of which is spatially spread out as a function of wavelength over a multiplicity of pixels within the array. This allows for a compact and inexpensive system with high light throughput.

The detected intensities of a plurality of pixels corresponding to the first order, and the detected intensities of pixels corresponding to the 0th order, may then be used to perform the necessary detection.

BRIEF DESCRIPTION OF THE DRAWINGS

The present invention can better be understood through the attached figures in which.

DETAILED DESCRIPTION OF THE PREFERRED EMBODIMENT

Figure 1:
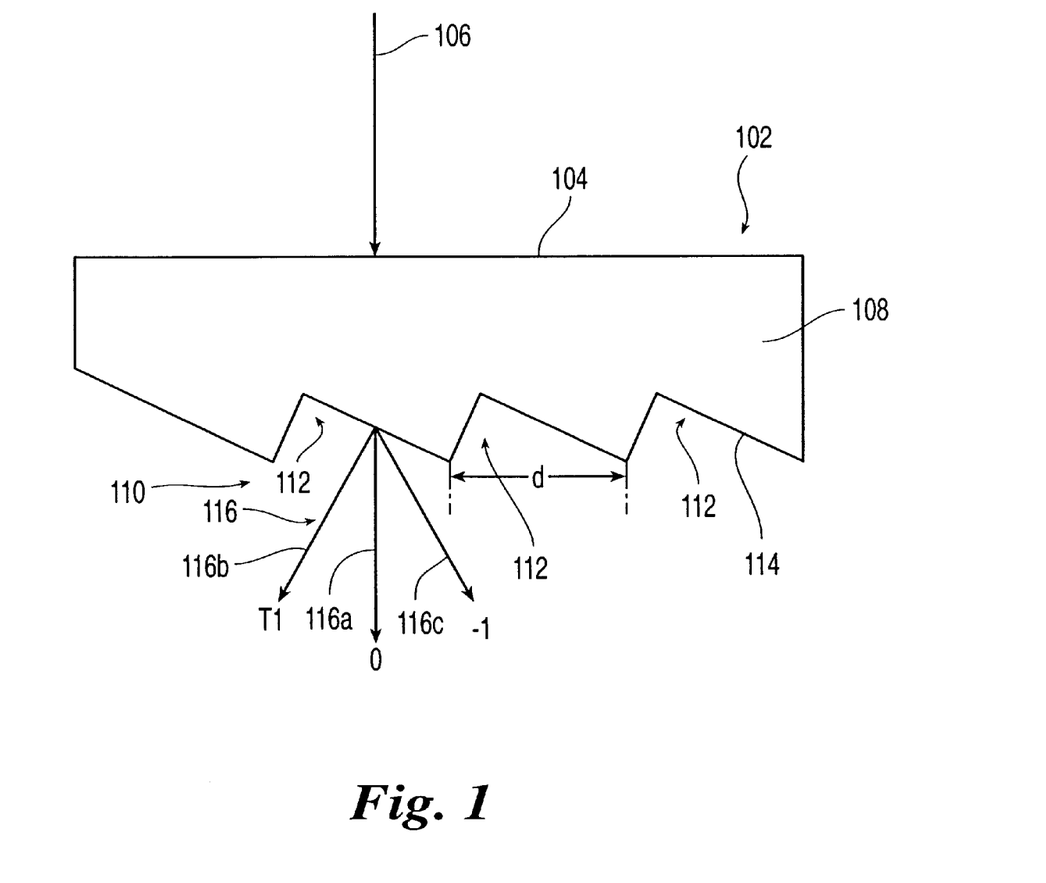
FIG. 1 shows a transmission grating beam splitter, such as that used in the present invention.

FIG. 1 shows a typical transmission grating beam splitter (TGBS) 100 of the sort used in the present invention. The TGBS of FIG. 1 has a first side 102 formed with an incident surface 104 on which incoming light 106 impinges, a substantially transparent body 108 through which the incoming light passes, and a second side 110 from which the split light emerges. As shown in FIG. 1, the second side 110 is provided with a plurality of grooves 112 having a width d, each groove being provided with an angled exit surface 114 forming a wall of that corresponding groove.

The incident light 10 passes through the first surface 104, the body 108, and emerges as a split beam 116 from one of the angled exit surfaces 114. As seen in FIG. 1, the split beam comprises a 0th order beam 116a, a +1 order beam 116b and a −1 order beam 116c.

As is known to those skilled in the art, a TGBS is typically formed from quartz, or other suitable, substantially transparent material selected for its index of refraction. The behavior of a TGBS is described in technical note TN 35-51 entitled "Transmission Gratings", published by the Richardson Grating Laboratory Division of the Milton Roy Company of Rochester, N.Y.

Figure 2A:
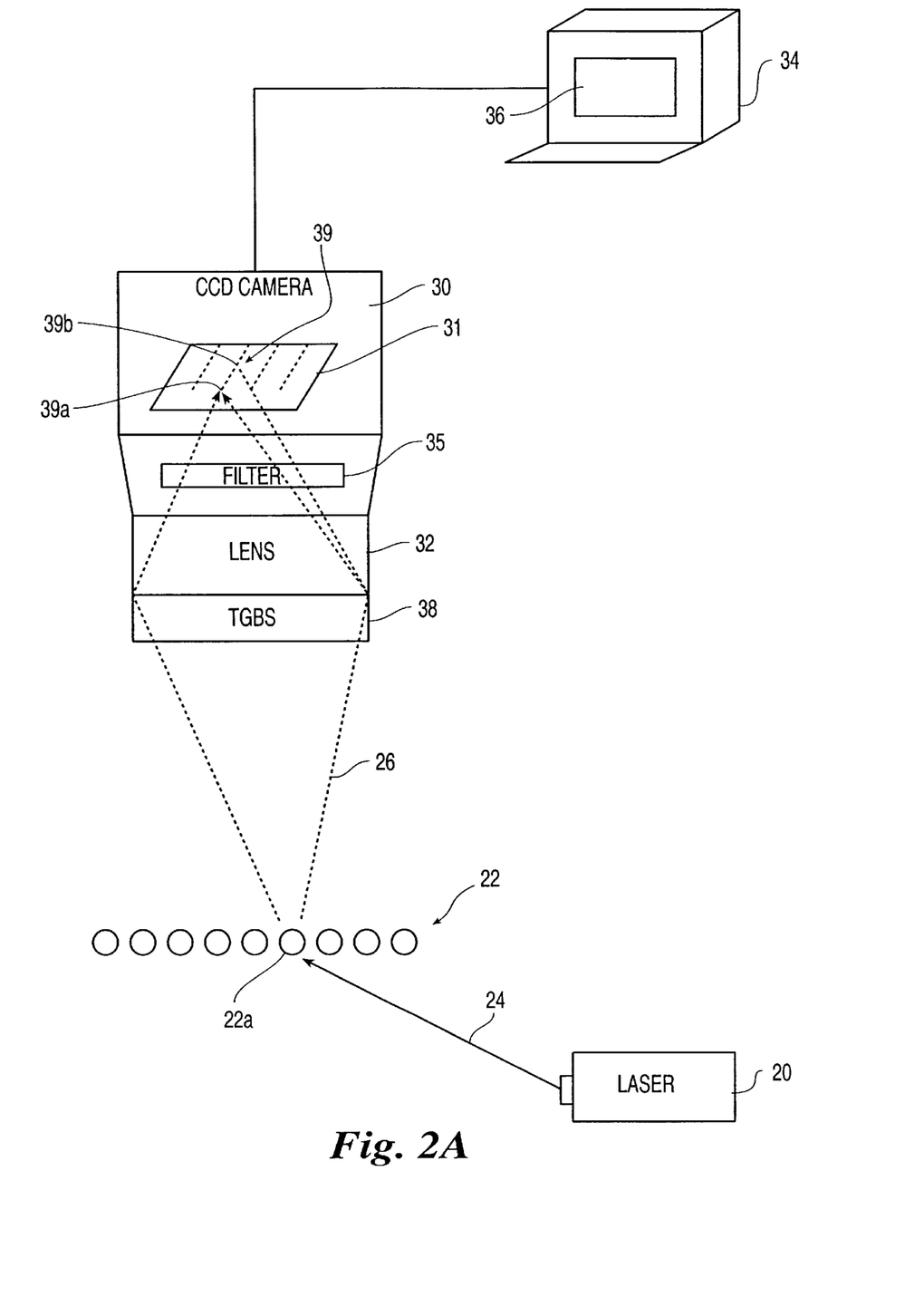
FIGS. 2a & 2b show two embodiments for a detector in accordance with the present invention.

FIG. 2a shows the environment and preferred arrangement of the present invention. A laser 20 is used to illuminate a row of capillary tubes 22 which extend parallel to one another, out of the plane of FIG. 2a. The capillary tubes contain a gel in which fluorophore-tagged DNA molecules are migrating during capillary electrophoresis. The capillaries 22, available from PolyMicro Technologies, are approximately 75 cm long and have an inner diameter of 75 $\mu$m and an outer diameter of between 150–250 $\mu$m.

In the preferred embodiment, the laser 20 is an 100 mW air cooled Argon ion laser, available from Spectra Physics. The laser outputs monochromatic light 24 at 488 nm. Alternatively, an Argon ion laser emitting a plurality of discrete wavelengths between, for instance, 460–514 nm may be used. In either case, the laser light 24 is focused onto the row of capillary tubes 22. As shown in FIG. 2a, the laser light is directed at an acute angle relative to the plane formed by the row of capillary tubes 22, rather than being directed normal thereto. Preferably, this angle is on the order of 10–30° relative to the plane, and thus 60–80° relative to the normal. For a row of 96 capillaries, each having an outer diameter of about 200 μm, the laser light 24 would have to illuminate a total width of approximately 2 cm to cover all the capillaries.

When the capillaries 22 are illuminated by the laser 20, the fluorophore-tagged DNA molecules fluoresce and produce an incoming light 26, represented by broken lines, directed towards the CCD camera 30. In the preferred embodiment, the camera 30 is a SpectraVideo #ST001E, available from PixelVision of Beaverton, Ohio. The camera 30 has a rectangular detector array 31 comprising 165 rows and 1100 columns of 16-bit pixels. From the detector array 31 within the camera 30, the detected intensities are sent to a processing unit, such as a personal computer 34, or like, having a display 38 and associated memory storage (not shown). Before reaching the detector array 31, the incoming light 26 passes through additional lens and spectral filtering elements. In the preferred embodiment, the light first passes through a 28 mm, f 1.4 Nikon lens 32. Later on, the light also passes through a filter 35 before impinging on the detector array 31. The purpose of the filter 35 is to allow fluorescent light of interest to pass therethrough, while attenuating light in wavelengths not of fluorescent interest, such as the wavelengths emitted by the laser 20. Examples of filters which may be used include a Raman notch filter, available from Kaiser Optical Systems of Ann Arbor, Mich., and a longpass filter having a cut-off of 515 nm, available from Spinder & Hoyer Inc., of Milford, Mass. In general, one may use filters which pass wavelengths at which fluorescence of interest is expected, and block wavelengths at which no fluorescence of interest is expected. For instance, one may wish to block the wavelength of the laser light 24 from the laser 20.

However, before reaching the detector array 31 within the camera 30, the incoming light 26 first passes through a transmission grating beam splitter 38 ("TGBS"). In the preferred embodiment, the TGBS is a Model #P46,068, available from Edmund Scientific of Barrington; N.J. This particular TGBS measures approximately 1"×1", although other sizes and shapes can be used. As shown in FIG. 2a, the TGBS, the lens and the filter are all attached to the camera 30, thus obviating the need for freestanding optical elements.

Figure 2B:
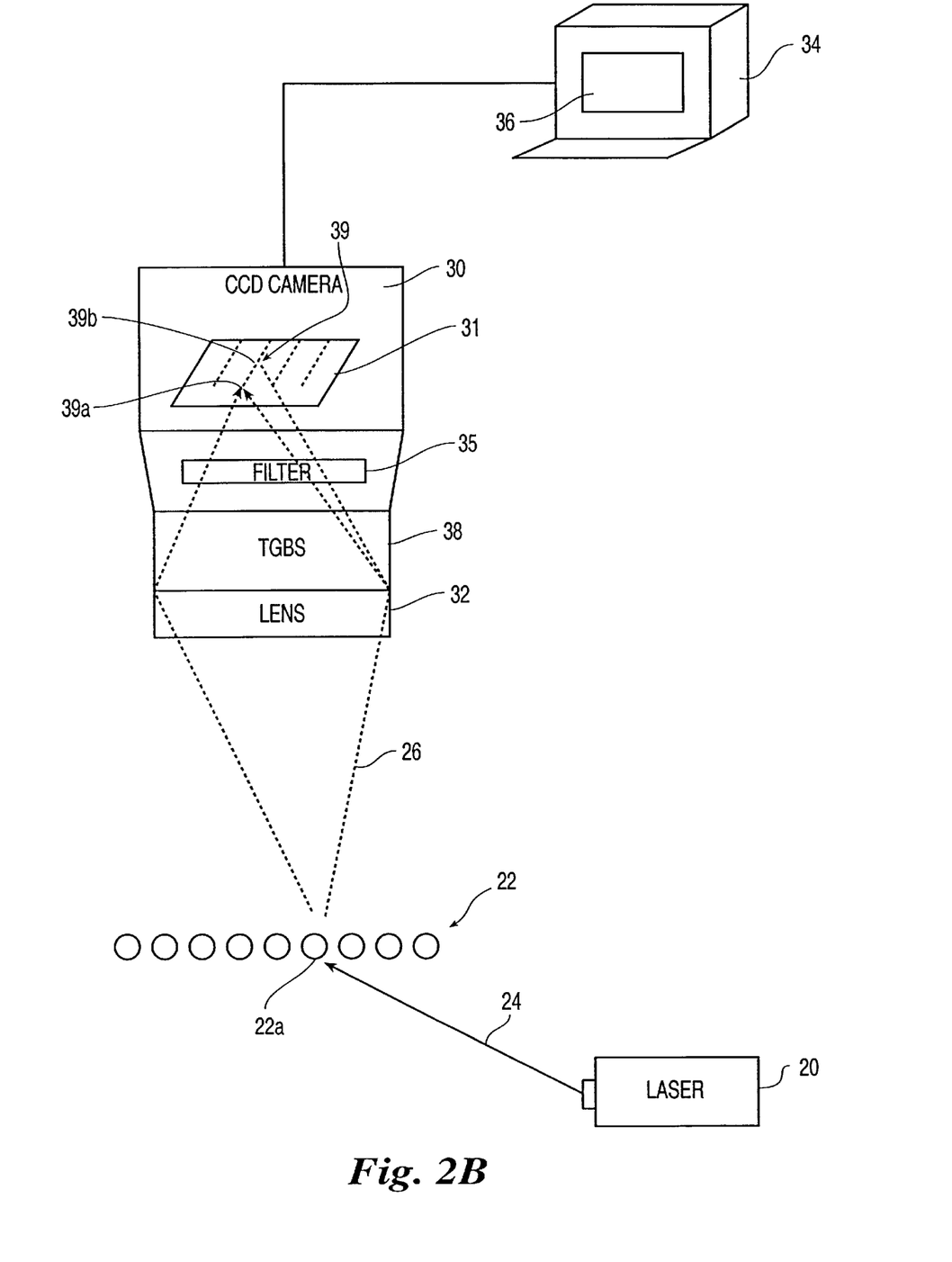

FIG. 2b depicts an alternate embodiment in which the TGBS is positioned between the lens 32 and the filter 35. In such case, the TGBS may be integrated into the camera 30, or be fixed in some manner to the lens 32. In this alternate embodiment, the spacing between the capillaries 22 and the camera lens is about 3 cm, the spacing between the camera lens and the TGBS about 0.5 cm and the spacing between the TGBS and the detector array 31 is about 4 cm. As is known to those skilled in the art, these spacings depend on the focal length of the lens, and the thicknesses of the optical components. It is noted that a TGBS normally requires substantially parallel, or collimated, incoming light. Thus, in the embodiment of FIG. 2b, the lens 32 has a long focal length so that the light impinging on the TGBS 38 is substantially parallel.

When using the detector system of FIG. 2b, the laser beam from laser 20 is set to a width (in the dimension coming out of FIG. 2b) of about 100–500 μm, and a length sufficient to extend along the breadth of the row of capillaries 22. This causes the samples in each of the capillaries to fluoresce, effectively causing a linear series of fluorescence spots. The camera lens focuses this linear series onto a detector array of the camera.

The fluorescence light 26 from the samples within the row of capillaries 22 is collected by the camera lens from a wide solid angle, and this light is focused onto the CCD. In the embodiments of both FIGS. 2a and 2b, the light is dispersed within the TGBS, and emerges with spectral components of different orders, with the first order having the greatest intensity and dominating over the other orders. This provides a light collection efficiency which is greater than that of a prior art fluorometer having an entrance slit and collimator lenses. The separated, fluoresced light from a given capillary 22a is detected by pixels of a particular column 39 of the array 31, with the 0th order component being detected by a first pixel 39a and the 1st order component being detected by at least one of a plurality of second pixels 39b, spaced apart from the first pixel.

Figure 3A:
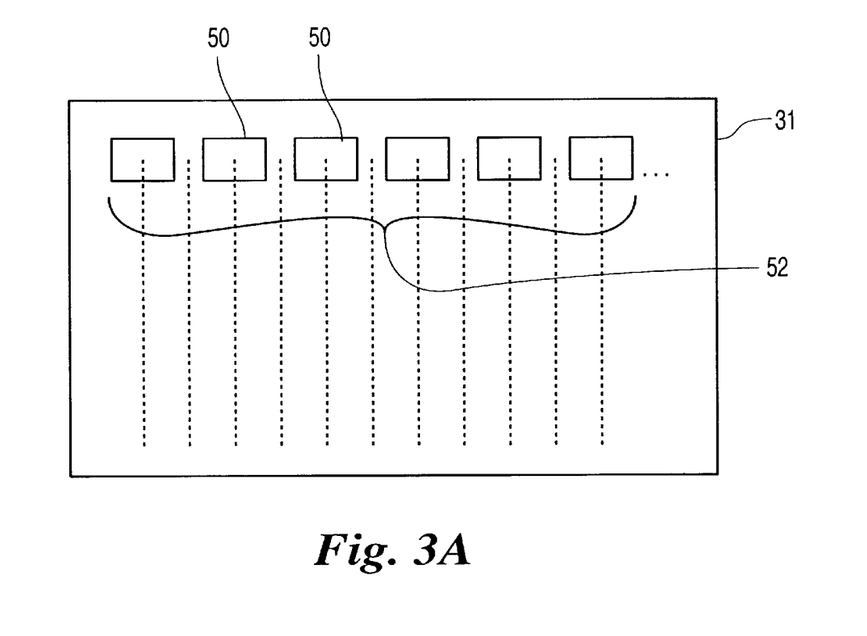
FIG. 3a shows detector array output with a detector not having a transmission grating beam splitter.

FIG. 3a illustrates the effect of using a detector system of the present invention, but with the TGBS omitted. In the absence of the TGBS, each capillary creates a single fluorescence spot 50 on the detector array 31, and all the capillaries together form a row 52 of discrete florescence spots. Nothing else appears on the detector array 31.

Figure 3B:
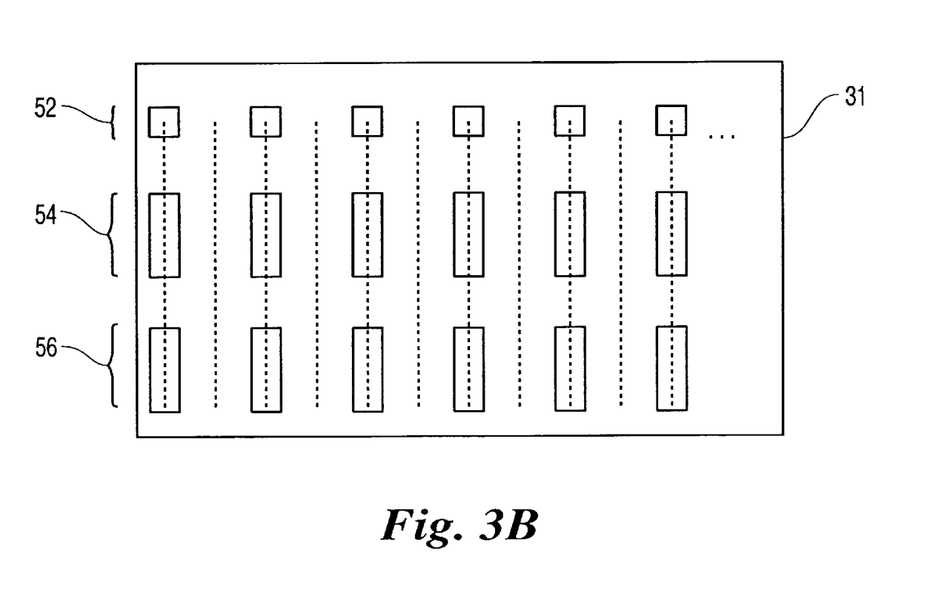
FIG. 3b shows detector array output with a detector having a transmission grating beam splitter.

FIG. 3b illustrates the effect of using a detector system of the present invention with the TGBS included. When the TGBS is inserted into the system, the florescence from the capillaries 22 is split into a plurality of bands, each band representing a particular order. Thus, FIG. 3b depicts the formation of a 0th order band 52, a 1st order band 54 and a 2nd order band 56. When imaged onto a detector array, each of these bands occupies a plurality of rows of pixels in the vertical direction, with different capillaries being imaged onto different columns, at least one column of pixels for each capillary. The 0th order band collects the fluorescence from all wavelengths and the members in this band are tightly focused, extending over only one or two rows of pixels for each column corresponding to a capillary. By contrast, the members in the 1st and 2nd order bands are dispersed, and extend over several rows pixels, along the column(s) corresponding to each capillary.

To facilitate subsequent processing of the light collected by the detector array, it is preferable that the 0th order bands from the capillaries are imaged onto the same row(s) of pixels, and that their corresponding 1st order bands are imaged onto substantially the same column(s). This alignment obviates the need to later correct for any skew among the received pixels in the sensed image, during subsequent processing. To ensure this, however, one typically may need to rotate the camera, and thus the detector array therein, relative to the row of capillaries.

It should be noted here that TGBSes can be selected to favor one or more orders over others. In other words, the transmittance in the favored orders can significantly exceed the transmittance in the disfavored orders. Thus, one may produce a TGBS which passes primarily 0th and 1st order components, while −1st order and other orders are considerably attenuated. The P46,068 model TGBS used in the preferred embodiment is such a 0th and 1st order-favoring device.

In the preferred embodiment, the transmission grating beam splitter has 70 grooves/mm. The angular difference between the 0th and 1st order is about 2°, and the dispersion angle within the 1st order for wavelengths between 500 nm and 700 nm is only about 0.8°. Thus, the 0th and 1st orders for a single capillary can easily be separated from one another on a detector array having a pixel width of about 25 μm, by judiciously spacing the TGBS from the plane of the array.

Figure 4A:
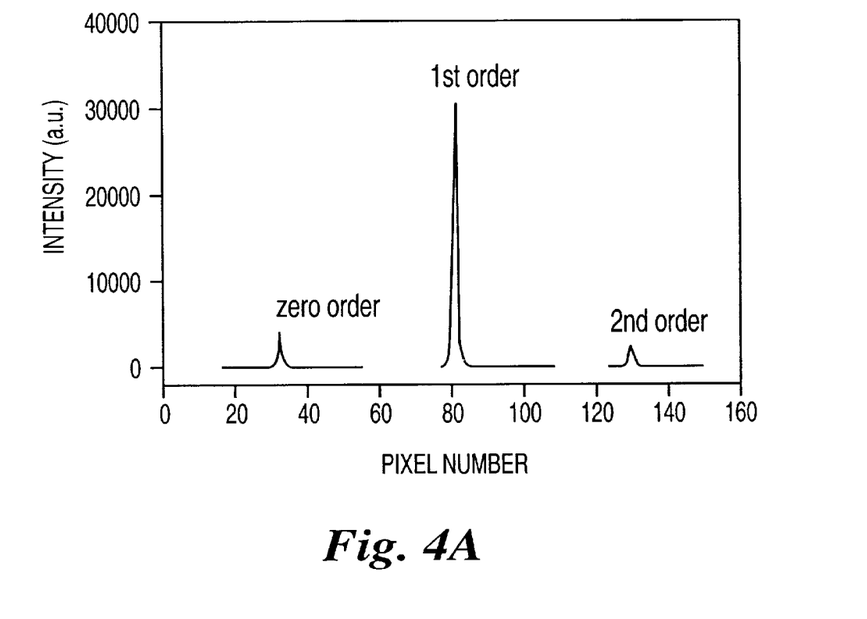
FIGS. 4a and 4b show the response of a detector of the present invention to monochromatic light with a target capillary present.

FIG. 4a shows the relative separation between, and spread of, the 0th, 1st and 2nd orders scattered by a single capillary with the resultant light impinging on a lens/TGBS/detector array arrangement not having the filter 35. The laser light is focused to a small spot occupying an area of 2×2 pixels on the detector array. Thus, this image represents the detector's system response. The intensity distribution of 0th, 1st and 2nd orders is about 1, 7 and 0.6, respectively.

Figure 4B:
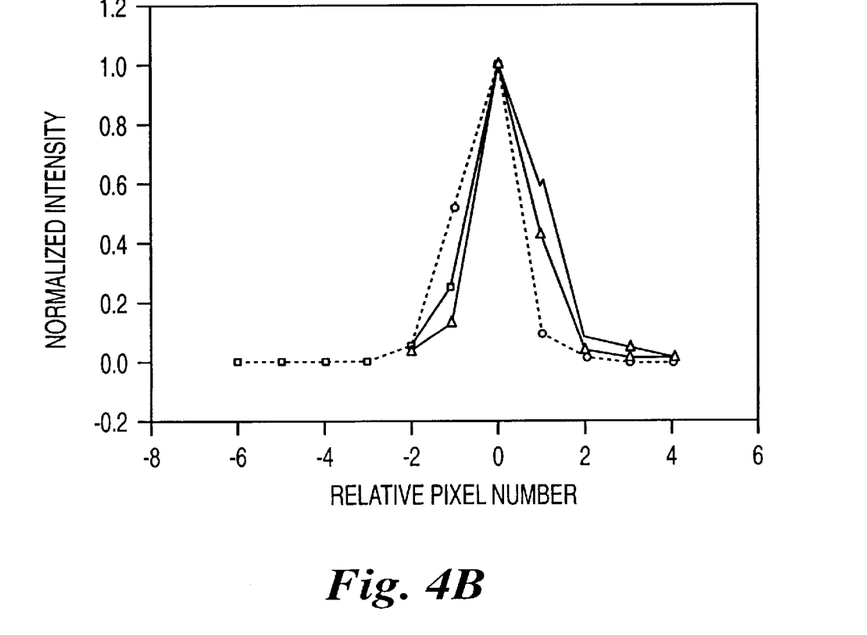

FIG. 4b shows an expanded view of the peaks corresponding to 0th, 1st and 2nd order in FIG. 4a, after normalizing each to an intensity of 1.0, and co-locating them. This figure shows that the spread for each of the peaks in response to monochromatic light is substantially same for each order. In particular, the widths of each peak at half normalized maximum intensity are substantially similar, given the 1-pixel detector resolution. Thus, the image dispersion of the present detector is negligible for 0th, 1st and 2nd orders using monochromatic light.

Figure 5:
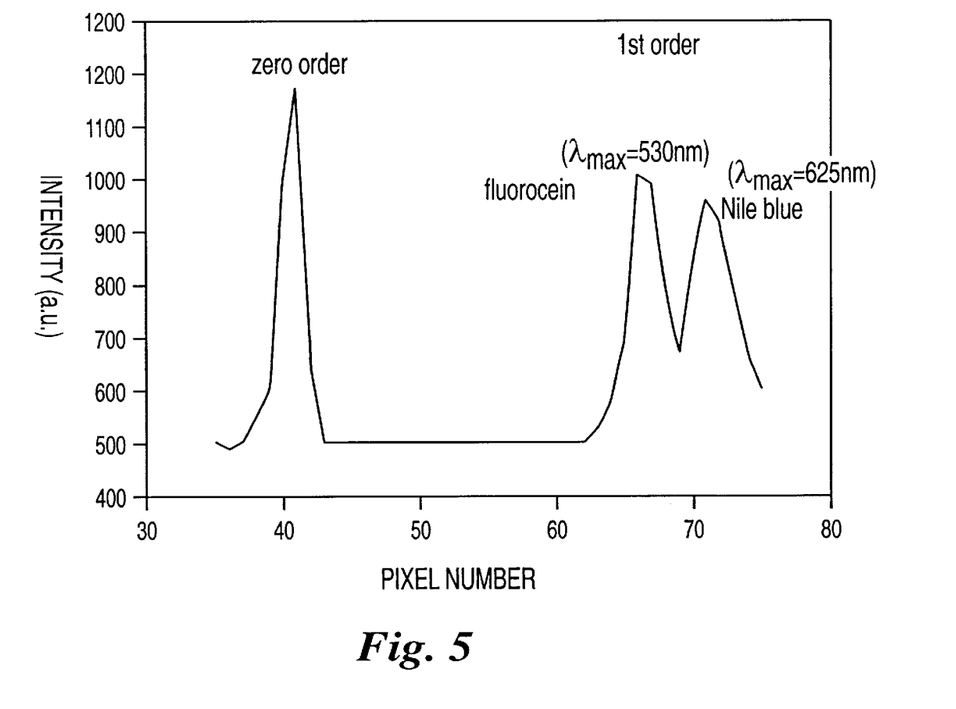
FIG. 5 shows the response of a detector of the present invention with a capillary containing two dyes.

FIG. 5 shows the output from illuminating a capillary carrying two dyes, fluorescein ($\lambda_{max}$=530 nm) and nile blue ($\Lambda_{max}$=625 nm), using the detector of the present system. Both the 0th order and the 1st order peaks appear, and distinct 1st order peaks appear for each of the two dyes. The 0th order confines all wavelengths of fluorescence within one or two pixels in the detector array. In contrast, the 1st order disperses the fluorescence from the two dyes across multiple pixels.

Figure 6A:
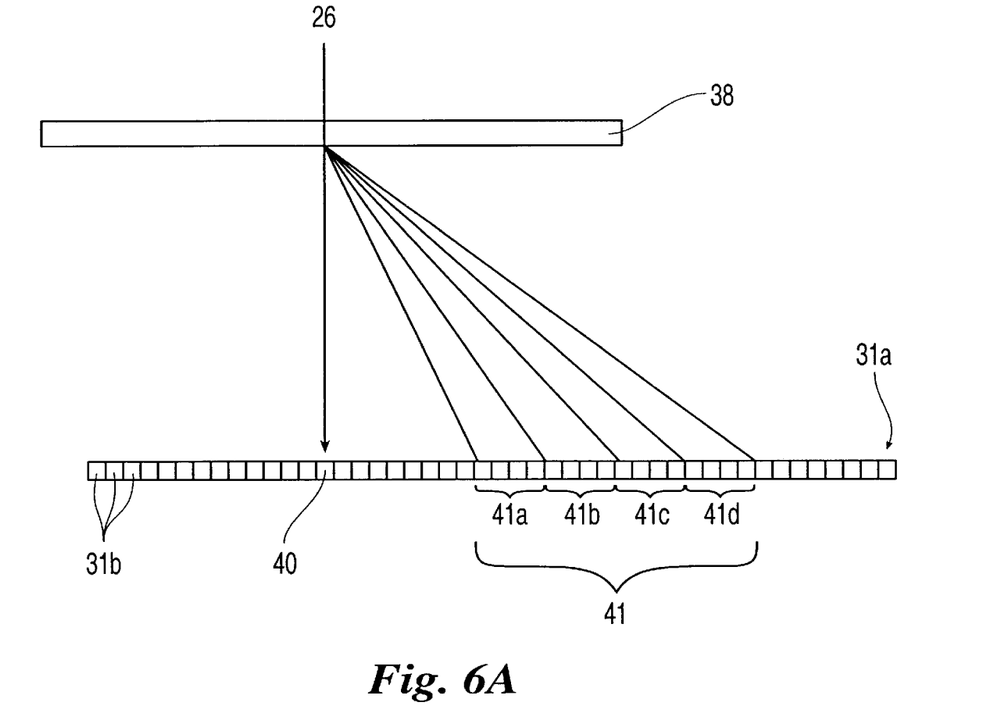
FIGS. 6a and 6b shows a transmission grating beam splitter separating incoming light comprising four wavelength bands.
Figure 6B:
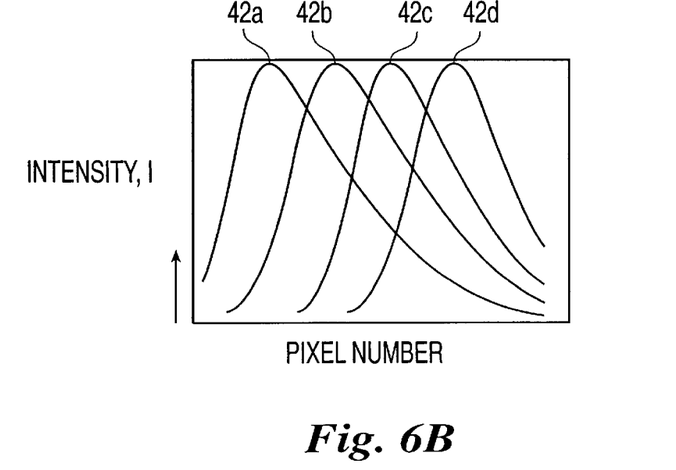

FIGS. 6a and 6b show the effect of a detector in accordance with the present invention on incoming light 26 from tagged DNA samples of a single capillary. For simplicity, only the TGBS 38 and one pixel column 31a of the detector array 31, comprising a plurality of pixels 31b, is shown in FIG. 6a. It is understood, however, that the lens 32 can be interposed between the TGBS and the pixel column 31a, or, as described above, the incoming light 26 may have already passed through the camera lens 32 at this point.

The incoming light 26 is separated into a 0th order component 40 and a 1st order component 41. As shown in FIG. 6a, the 0th and 1st order components are spatially separated from each other, as they impinge on the pixel column 31a. This separation will subsequently allow one to use the intensities of both the 0th order and the 1st order transmitted incoming light components when performing subsequent analyses for identifying particular fluorophores, and hence, the corresponding nucleotides.

As is known to those skilled in the art of DNA sequencing using capillary electrophoresis, each of the four DNA nucleotides are typically tagged with one of four fluorophores which fluoresce in overlapping wavelengths. Thus, in FIG. 6a, the detected 1st order light 41 comprises four sub-bands, designated 41a, 41b, 41c and 41d, each corresponding to a region along the column of pixels 31a, in which a particular one of the four fluorophores dominates.

FIG. 6b shows the relative intensity of fluorescence of the four fluorophores as a function of relative pixel number. Here, increasing pixel number corresponding to increasing wavelength. In FIG. 6b, curves 42a, 42b, 42c and 42d correspond to the fluorescence emission spectra of the four fluorophores, each of which is shown to be dominant in a corresponding one of the four pixel regions 41a, 41b, 41c and 41d of FIG. 6a.

As stated above, in FIG. 6a, the pixel column 31a corresponds to the detector output for a single capillary. And for that one capillary, data is available for a number of contiguous pixels, including a small number of pixels which have 0th order information, and a larger number of pixels which have 1st order information. This offers some flexibility in performing subsequent analysis to determine exactly which fluorophore is present at any given time.

Figure 7:
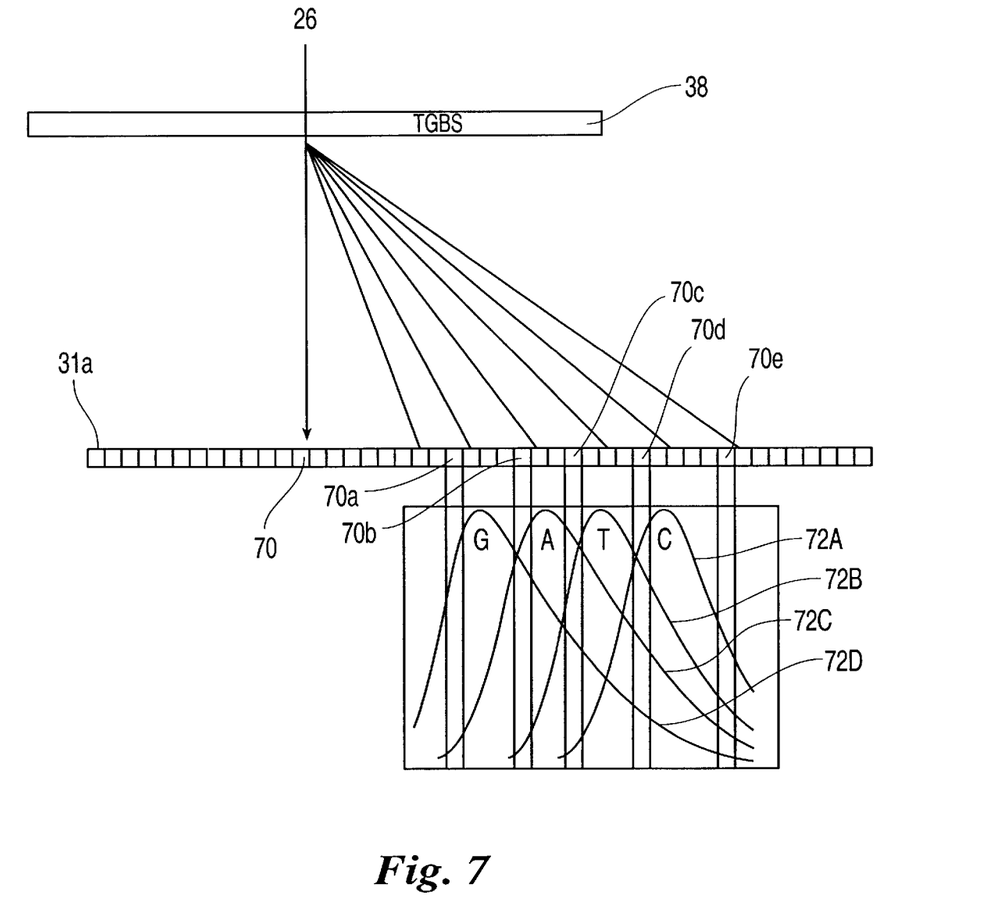
FIG. 7 presents a pixel sampling scheme for identifying nucleotides with a detector of the present invention.

FIG. 7 shows how the pixels of the pixel column 31a may be sampled to come up with a detection scheme which exploits the detector of the present invention. In the preferred embodiment, six pixels are monitored. Pixel 70 corresponds to the 0th order component, and pixels 70a, 70b, 70c, 70d and 70e correspond to various portions of the first order component.

In this example, fluorophores, whose spectral curves are given by 72a, 72b, 72c and 72d, each tag a specific nucleotide, Guanine ("G"), Adenosine ("A"), Thymine ("T") and Cytosine ("C"), respectively.

Pixel 70a is positioned slightly to the left of the peak for nucleotide G. Thus, it receives much energy contribution from G, and virtually none from the A, T and C. Thus, energy in pixel 70a indicates the presence of G.

Pixel 70b is positioned roughly at the intensity cross-over point between fluorophores which correspond to nucleotides G and A. Thus, signal energy from pixel 70b gets substantially equal contribution from these two nucleotides, and very little from T and C. Thus, energy in pixel 70b indicates the presence of either G or A.

Pixel 70c is positioned near the intensity cross-over point for nucleotides A and T. Pixels 70c receives somewhat less contribution from G, and virtually no contribution from C. Thus, energy in pixel 70c is indicative of A or T, and, to a lesser extent, of G.

Pixel 70d is positioned near the intensity cross-over point for nucleotides T and C. This pixel receives nearly equal contribution from these two nucleotides, somewhat less from A, and considerably less from G. Thus, energy in pixel 70d is indicative of T or C, of A to a slightly lesser extent, and of G to an even lesser extent.

Pixel 70e is positioned to the right of the intensity peak for nucleotide C. At this point, there is relatively little contribution from T, even less from A, and still less from G. Thus, strong energy presence in pixel 70e is indicative of C.

In practice, these six pixels, 70 and 70a–70e are monitored continuously as electrophoresis takes place in at least one capillary tube. Migration along the capillary tube typically brings one nucleotide every 2–4 seconds, and the detector array is sampled every one-half or so seconds. Thus, a time series of the signal energy of each of these pixels can be used to derive the sequence of nucleotides passing through a window region of the capillary tube.

Figure 8:
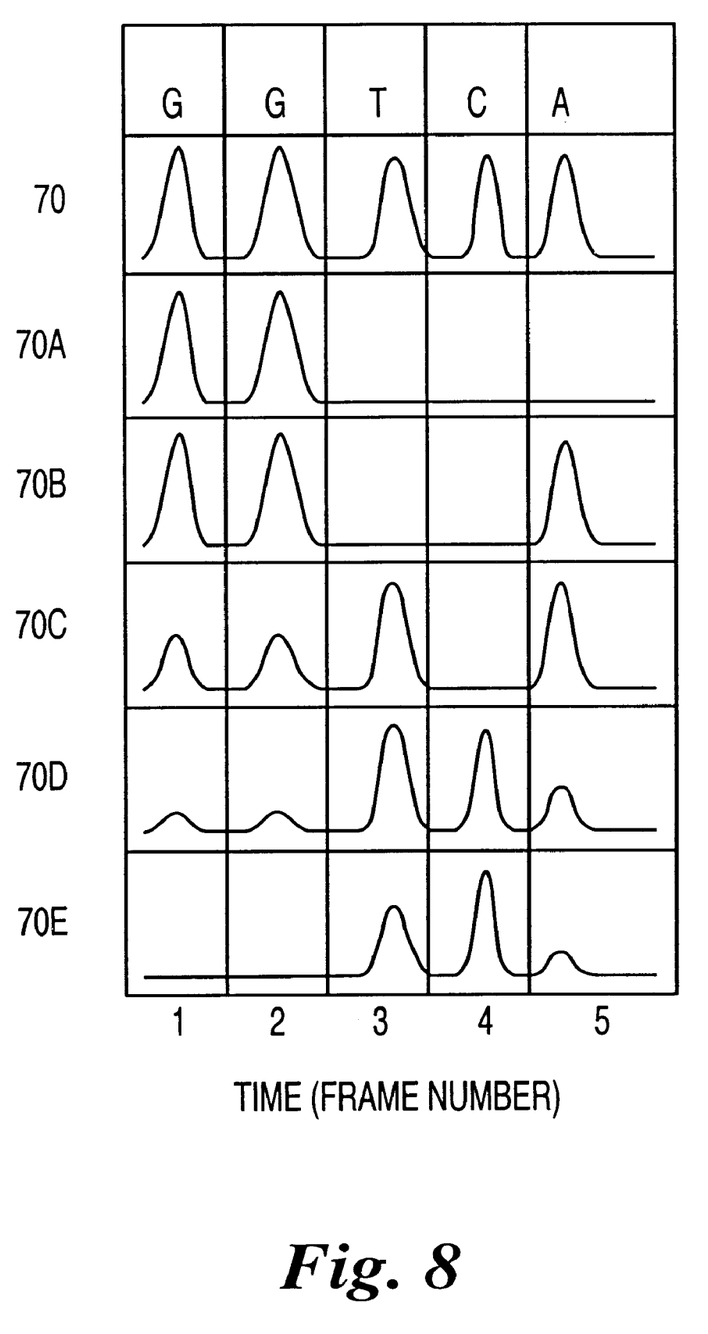
FIG. 8 presents synthetic data from the pixel sampling scheme of FIG. 7.

FIG. 8 shows a synthetic time series in which hypothetical pixel values for pixels 70a–70e are presented for the given set of nucleotides, each nucleotide causing one or more peaks among the 1st order pixels for each frame number, each frame number corresponding to the position at which a nucleotide is expected. Pixel 70, which corresponds to the 0th order time series, shows a peak each time a nucleotide is present. In contrast, the time series for the other pixels 70a–70e, which are normalized amongst themselves for each time frame, exhibit regions devoid of peaks, and show varying signal intensities, depending on the nucleotide present during that time frame.

DNA sequencing can be performed with the time series shown in FIG. 8 by simultaneously examining the intensities of all six pixels, during each time frame. For any given time frame, the presence of a signal in pixel 70 (0th order), indicates the presence of a nucleotide. Similarly, for each time frame, a strong signal in pixel 70*a* indicates G; a strong signal in both pixels 70*b* and 70*c* indicates A, a strong signal in both pixels 70*c* and 70*d* indicates T, and a strong signal in pixel 70*e* indicates C.

The time series data of FIG. 8 may be used in slightly different ways for DNA sequencing. For instance, for each time frame, the time series data for pixels 70*a*–70*e* may first be normalized by the 0th order value for that time frame, and the thus globally normalized values may be directly compared in lieu of searching for co-occurrences of signal peaks in multiple pixels, for each time frame.

Also, as stated above, TGBSes may be obtained which weight the 0th and 1st orders in different ways. Thus, with an appropriately weighted 0th and 1st order components, it may even be possible to convert the detected signal intensities of the selected pixels into logarithms through the use of a look-up table, and then subtract these from one another, in preparation for nucleotide identification. This approach may be especially useful if special purpose hardware were employed to implement the detection schemes.

It should be noted that the methodology of the present invention is independent of the particular set of fluorophores being used. Given a new set of fluorophores, one can derive their spatio-spectral characteristics using known techniques with a predetermined excitation wavelength, and then designate appropriate pixels for a detection scheme. It should also be noted that the present detection scheme provides one with more measured values (six) than unknowns (four nucleotides), and contrasts with known ratio-based methods which require solution of underdetermined systems. Indeed, the present detection scheme is not even limited to four fluorophores, since a first number of such fluorophores may be used to detect a second number of nucleotides, given appropriate sampling of the first order pixel components.

Figure 9:
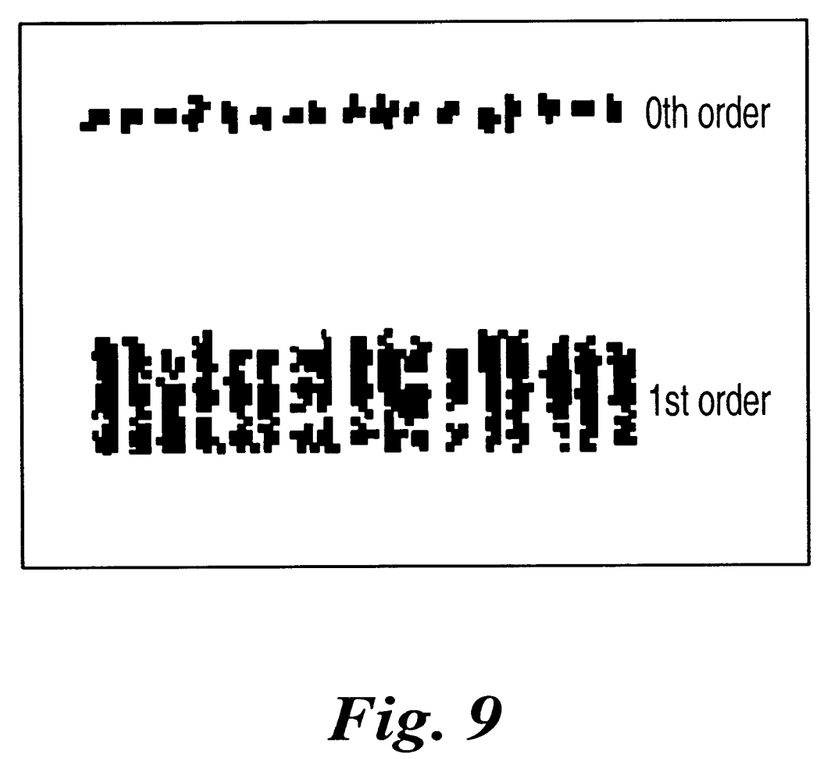
FIG. 9 presents experimental data which shows 0th and 1st order components using a 16 capillary trial run.

FIG. 9 is a sample display output from an actual trial using 16 capillaries containing DNA samples tagged with one of four dyes. These figures show the 0th and 1st order components from the trial, for a specific instant during electrophoresis. As can be seen in these figures, the 0th order band comprises compact members which do not extend much along the vertical axis of the display. On the other hand, the members of the 1st order band extend in this direction, testifying to the spreading of 1st order data along this dimension. However, it is important to note that the 0th order and the 1st order do not overlap.

Thus, a detector in accordance with the present invention simultaneously acquires the 0th and 1st order of the transmitted florescence pattern with suitable relative intensity for detection by a CCD, or other, detector. The 0th order light contains the whole wavelength of undispersed fluorescence from a target fluorophore going through a detection window of one or more capillaries. The 0th order light for all capillaries is collected by only one detector channel. Typically, this channel comprises at least one row of pixels in a CCD array, the number of pixels in each row corresponding to at least the number of capillaries. Meanwhile, the 1st order light is dispersed over a number of detector channels (typically a number of rows of pixels). The different detector channels (i.e., CCD rows in the preferred embodiment) represent different wavelength portion of the fluoresced light and are collected individually. The availability of both 0th (whole incoming fluoresced light) and 1st order data (partial incoming fluoresced light) allow for flexibility in subsequent data analysis In addition, a detector having a TGBS has three advantages over current used spectrograph-based techniques. First, the detector of the present invention has higher incoming light collection efficiency than a spectrograph, as the light throughput in a TGBS-based detector is determined only by the camera lens. This contrasts with a spectrograph, which employs a reflective grating system, which is typically not configured to retain the 0th order light energy. Second, a detector using a TGBS allows one to dispense with the bulkiness and high cost associated with a spectrograph, thereby resulting in a less expensive and miniaturized system, having greater flexibility and reliability. And third, a TGBS-based detector system has negligible image distortion when compared to the output from a spectrograph with its slits and collimating optics.

While the above invention has been described with reference to certain preferred embodiments, it should be kept in mind that the scope of the present invention is not limited to these. For instance, a compound lens may be used, and the filter may be placed between the lens and the TGBS, or even before both of them. Also, the samples may be illuminated by the laser after emerging from the capillary tubes following migration, rather than while they are still within the capillary tubes. Thus, one skilled in the art may find variations of these preferred embodiments which, nevertheless, fall within the spirit of the present invention, whose scope is defined by the claims set forth below.

What is claimed is:

1. An apparatus for detecting a light emitting species, said apparatus comprising:

a light source arranged to emit a light beam in a direction of said light emitting species, said light beam causing said light emitting species to output emitted light;

a light detector for sensing said emitted light, said light detector comprising:

a detector array comprising a plurality of pixels, each pixel arranged to measure an intensity of light impinging thereon;

a filter positioned between said detector array and said light emitting species;

a lens positioned between said detector array and said light emitting species, said lens selected and arranged to focus said emitted light onto said detector array;

a transmission grating beam splitter (TGBS) positioned between said detector array and said light emitting species, said TGBS separating said emitted light from said light emitting species into light components, wherein said emitted light passes through said transmission grating beam splitter without first being collimated; and computer means connected to said light detector to receive and process information representative of said light components.

2. The detector of claim 1, wherein the TGBS is positioned between the lens and the detector array.

3. The detector of claim 1, wherein the lens is positioned between the TGBS and the detector array.

4. The apparatus of claim 1, wherein said detector array is two-dimensional, comprising a plurality of row and columns of pixels.

5. The apparatus of claim 4, wherein said TGBS separates said emitted light into at least $1^{st}$ order light components, contiguous pixels within said detector array being configured to receive at least some of said $1^{st}$ order light components, a position of one of said contiguous pixels relative to others of said contiguous pixels being reflective of a wavelength of a $1^{st}$ order light component received by said one of said contiguous pixels.

6. The apparatus of claim 1, wherein said TGBS separates said emitted light into at least $1^{st}$ order light components, contiguous pixels within said detector array being configured to receive at least some of said $1^{st}$ order light components, a position of one of said contiguous pixels relative to others of said contiguous pixels being reflective of a wavelength of a $1^{st}$ order light component received by said one of said contiguous pixels.

7. The apparatus of claim 1, further comprising a plurality of capillaries along which said light emitting species migrate.

8. A light detector for simultaneously sensing fluoresced light from a first number of fluorophores spaced apart from one another, said light detector comprising:

a two-dimensional detector array comprising a plurality of rows and columns of pixels, each pixel arranged to measure an intensity of light impinging thereon, the number of columns in said detector array exceeding said first number;

a filter positioned between said detector array and said fluorophores, said filter selected and arranged to block light of at least one predetermined wavelength from reaching said detector array;

a lens positioned between said detector array and said fluorophores, said lens selected and arranged to focus said fluoresced light onto said detector array;

a transmission grating beam splitter (TGBS) positioned between said detector array and said fluorophores, said TGBS separating said fluoresced light from said fluorophores into at least 1st order light components, wherein said fluoresced light passes through said transmission grating beam splitter without first being collimated; and wherein said 1st order light components from each fluorophore are received by a plurality of contiguous pixels, a position of one of said contiguous pixels relative to others of said contiguous pixels being reflective of a wavelength of $1^{st}$ order light component received by said one of said contiguous pixels.

9. The detector of claim 8, wherein the TGBS is positioned between the lens and the detector array.

10. The detector of claim 8, wherein the lens is positioned between the TGBS and the detector array.

11. The apparatus of claim 8, further comprising a plurality of capillaries along which said fluorophores migrate.

12. An apparatus for detecting a first number of light emitting species which have migrated along a medium, said apparatus comprising:

a light source arranged to emit a light beam having at least one predetermined wavelength in a direction of said light emitting species, said light beam causing each of said light emitting species to output an emitted light;

a light detector for simultaneously sensing said emitted light from said first number of light emitting species, said light detector comprising:

a two-dimensional detector array comprising a plurality of rows and columns of pixels, each pixel arranged to measure an intensity of light impinging thereon, the number of columns in said detector array exceeding said first number;

a filter positioned between said detector array and said light emitting species, said filter selected and arranged to block light of at least one predetermined wavelength from reaching said detector array;

a lens positioned between said detector array and said light emitting species, said lens selected and arranged to focus said emitted light onto said detector array;

a transmission grating beam splitter (TGBS) positioned between said detector array and said light emitting species, said TGBS separating said emitted light from said light emitting species into at least 1st order light components, wherein said emitted light passes through said transmission grating beam splitter without first being collimated; and wherein said 1st order light components from each light emitting species are received by a plurality of contiguous pixels, a position of one of said contiguous pixels relative to others of said contiguous pixels being reflective of a wavelength of a $1^{st}$ order light component received by said one of said contiguous pixels; and computer means connected to said light detector to receive and process information representative of the 1st order light components received by said pixels.

13. The apparatus of claim 12, further comprising a plurality of capillaries along which said light emitting species migrate.

* * * * *